(12) United States Patent
Guerin et al.

(10) Patent No.: US 7,857,865 B2
(45) Date of Patent: Dec. 28, 2010

(54) COMPOSITION COMPRISING AT LEAST ONE ORTHO-DIPHENOL, METAL SALT, HYDROGEN PEROXIDE AND (BI)CARBONATE AND HAIR DYEING METHOD THEREWITH

(75) Inventors: Frédéric Guerin, Paris (FR); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/637,236

(22) Filed: Dec. 14, 2009

(65) Prior Publication Data
US 2010/0150857 A1    Jun. 17, 2010

Related U.S. Application Data

(60) Provisional application No. 61/141,435, filed on Dec. 30, 2008.

(30) Foreign Application Priority Data
Dec. 12, 2008    (FR) .................................. 08 58557

(51) Int. Cl.
*A61Q 5/10*    (2006.01)
(52) U.S. Cl. ...................... 8/405; 8/406; 8/424; 8/435; 8/594; 8/629; 132/202; 132/208
(58) Field of Classification Search ...................... 8/405, 8/408, 424, 435, 594, 629; 132/202, 208
See application file for complete search history.

(56) References Cited

U.S. PATENT DOCUMENTS

| 4,801,302 | A | | 1/1989 | Grollier |
| 5,603,734 | A | * | 2/1997 | Prota et al. ..................... 8/424 |
| 6,953,486 | B2 | | 10/2005 | Pruche |

2003/0103917 A1   6/2003   Pruche

FOREIGN PATENT DOCUMENTS

| DE | 199 59 480 A1 | 6/2001 |
| DE | 10 2005 062 830 A1 | 1/2007 |
| EP | 0 124 393 A1 | 11/1984 |
| EP | 0 664 114 A1 | 7/1995 |
| FR | 2 598 318 A1 | 11/1987 |
| FR | 2 814 945 A1 | 4/2001 |
| FR | 2 814 946 A1 | 4/2001 |
| FR | 2 814 947 A1 | 4/2001 |
| FR | 2 814 943 A1 | 4/2002 |
| JP | 08 012539 | 1/1996 |

OTHER PUBLICATIONS

French Search Report for FR 0858557, dated Aug. 27, 2009.
French Search Report for FR 0858556, dated Aug. 19, 2009.
French Search Report for FR 0858555, dated Aug. 27, 2009.
French Search Report for FR 0858554, dated Aug. 19, 2009.
French Search Report for FR 0858558, dated Aug. 24, 2009.
English language abstract of DE 199 59 480 A1, Jun. 21, 2001.
English language abstract of DE 10 2005 062 830 A1, Jan. 4, 2007.
English language abstract of EP 0 124 393 A1, Jul. 11, 1984.
English language abstract of FR 2 814 943 A1, Apr. 12, 2002.
English language abstract of FR 2 814 945 A1, Apr. 12, 2002.
English language abstract of JP 08 012539, Jan. 16, 1996.
Co-pending Application filed Dec. 14, 2009.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The disclosure relates to a method for dyeing keratinous fibers by applying, to said fibers, i) at least one entity chosen from ortho-diphenol and derivatives thereof, ii) at least one metal salt, iii) hydrogen peroxide or at least one system which generates hydrogen peroxide, and iv) at least one (bi)carbonate, wherein the method for coloring keratinous fibers is carried out in at least two stages, and wherein the at least one (bi)carbonate and the at least one metal salt are applied in separate stages. The disclosure also relates to a ready-to-use cosmetic composition and relates to a multicompartment device comprising from 2 to 5 compartments comprising from 2 to 5 compositions.

19 Claims, No Drawings

COMPOSITION COMPRISING AT LEAST ONE ORTHO-DIPHENOL, METAL SALT, HYDROGEN PEROXIDE AND (BI)CARBONATE AND HAIR DYEING METHOD THEREWITH

This application claims benefit of U.S. Provisional Application No. 61/141,435, filed Dec. 30, 2008. This application also claims benefit of priority under 35 U.S.C. §119 to French Patent Application No. 0858557, filed Dec. 12, 2008.

The present disclosure relates to compositions, methods, and kits for dyeing keratinous fibers, such as compositions, methods, and kits making use of i) at least one entity chosen from ortho-diphenol and derivatives thereof, ii) at least one metal salt, iii) at least hydrogen peroxide or at least one system which generates hydrogen peroxide and iv) at least (bi)carbonate.

So-called "permanent" colorings can be obtained with dyeing compositions comprising oxidation dye precursors, generally known as oxidation bases, such as ortho- or para-phenylenediamines, ortho- or para-aminophenols and heterocyclic compounds. These oxidation bases can be colorless or weakly colored compounds which, in combination with oxidizing products, can give rise, by an oxidative coupling process, to colored compounds. The shades obtained can be varied by combining these oxidation bases with couplers or coloring modifiers, the latter being chosen, e.g., from aromatic meta-diamines, meta-aminophenols, meta-diphenols and certain heterocyclic compounds, such as indole compounds. This oxidation dyeing method can involve applying, to the keratinous fibers, bases or a mixture of bases and of couplers with hydrogen peroxide ($H_2O_2$ or aqueous hydrogen peroxide solution) as oxidizing agent, allowing diffusion to occur, and then rinsing the fibers. The colorings which result therefrom can be permanent, powerful and resistant to external agents, e.g., to light, bad weather, washing operations, perspiration and rubbing actions.

However, the commercial hair dyes which comprise them can exhibit disadvantages, such as staining or problems of smell, of comfort or of decomposition of the keratinous fibers. This can be the case with, for example, oxidation dyeing operations.

There exists a need to develop dyeing methods which make it possible to obtain powerful colorings starting from ortho-diphenols, such as by starting from a natural extract rich in ortho-diphenols, while limiting the decoloration of the keratinous fibers. There further exists a need to obtain colorings which are less aggressive to the hair and, at the same time, which can withstand external agents (light, bad weather, shampooing operations) and which can be persistent and homogeneous while remaining powerful and chromatic. The subject matter of the present disclosure, inter alia, can in some embodiments satisfy one or more of these needs.

An aspect of the present disclosure is a method for dyeing keratinous fibers comprising treating said fibers with:
i) at least one entity chosen from ortho-diphenol and derivative(s) thereof,
ii) at least one metal salt,
iii) hydrogen peroxide or at least one system which generates hydrogen peroxide, and
iv) at least one (bi)carbonate,
with the proviso that if the at least one system which generates hydrogen peroxide is used, then the at least one (bi)carbonate and the at least one metal salt are applied in separate stages.

Another aspect of the present disclosure is a ready to use cosmetic composition for dyeing keratinous fibers comprising
i) at least one entity chosen from ortho-diphenol and derivatives thereof,
ii) at least one metal salt,
iii) hydrogen peroxide or at least one system which generates hydrogen peroxide,
iv) at least one (bi)carbonate,
and water in an amount greater than or equal to 50% by weight of the total weight of the composition.

Another aspect of the present disclosure is a multicompartment device comprising from 2 to 5 compartments comprising from 2 to 5 compositions in which the ingredients
i) at least one entity chosen from ortho-diphenol and derivatives thereof,
ii) at least one metal salt,
iii) hydrogen peroxide or at least one system which generates hydrogen peroxide,
iv) at least one (bi)carbonate,
and water are distributed, the water being present in at least one of the said 2 to 5 compositions, the other 1 to 4 compositions being aqueous or pulverulent, and the water being present in a total amount greater than or equal to 50% by weight of the total weight of the 2 to 5 compositions.

The methods according to the disclosure can exhibit the benefit of dyeing human keratinous fibers with powerful and chromatic colorings which can be resistant to washing operations, to perspiration, to sebum and to light and which can be in addition long lasting without a detrimental change to said fibers. Furthermore, the colorings obtained using the methods of the disclosure can give homogeneous colors from the root to the tip of a fiber (that is, they can have low dyeing selectivity).

i) Ortho-Diphenol Derivative:

In some embodiments, the disclosure relates to an entity chosen from ortho-diphenol and derivatives thereof or a mixture of compounds comprising at least one aromatic ring, such as a benzene ring, comprising at least two hydroxyl (OH) groups carried by two adjacent carbon atoms of the aromatic ring. The ortho-diphenol derivative or derivatives according to the disclosure are not autoxidizable derivatives comprising an indole unit. More, they are other than 5,6-dihydroxyindole.

The aromatic ring can be a fused aryl ring or a fused heteroaromatic ring, i.e. a ring optionally comprising at least one heteroatoms, such as benzene, naphthalene, tetrahydronaphthalene, indane, indene, anthracene, phenanthrene, isoindole, indoline, isoindoline, benzofuran, dihydrobenzofuran, chromane, isochromane, chromene, isochromene, quinoline, tetrahydroquinoline and isoquinoline, said aromatic ring comprising at least two hydroxyl groups carried by two adjacent carbon atoms of the aromatic ring. In some embodiments, the aromatic ring of the ortho-diphenol derivatives according to the disclosure is a benzene ring.

A "fused ring" is understood to mean that at least two saturated or unsaturated and heterocyclic or nonheterocyclic rings exhibit a common bond, i.e. that at least one ring is placed side by side with another ring.

The entity chosen from ortho-diphenol and derivatives thereof according to the disclosure may or may not be salified, i.e., present as a salt. It can also occur in the aglycone form (without bonded sugar) or in the form of a glycosylated compound.

In some embodiments, the ortho-diphenol derivative i) represents a compound of formula (I) or one of its oligomers, in or not in the salified form:

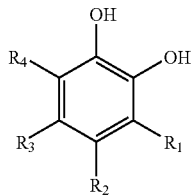

in which formula (I) the substituents:
$R_1$ to $R_4$, which can be identical or different, represent:
- a hydrogen atom,
- a halogen atom,
- a hydroxyl radical,
- a carboxyl radical,
- an alkyl carboxylate or alkoxycarbonyl radical,
- an optionally substituted amino radical,
- an optionally substituted linear or branched alkyl radical,
- an optionally substituted linear or branched alkenyl radical,
- an optionally substituted cycloalkyl radical,
- an alkoxy radical,
- an alkoxyalkyl radical,
- an alkoxyaryl radical, it being possible for the aryl group to be optionally substituted,
- an aryl radical,
- a substituted aryl radical,
- a saturated or unsaturated heterocyclic radical which does or does not carry a cationic or anionic charge, which is optionally substituted and/or which is optionally fused with an aromatic ring, such as a benzene ring, said aromatic ring being optionally substituted, e.g., by at least one hydroxyl or glycosyloxy group,
- a radical comprising at least one silicon atom;
- or two of the substituents carried by two adjacent carbon atoms $R_1$-$R_2$, $R_2$-$R_3$ or $R_3$-$R_4$ form, together with the carbon atoms carrying them, a saturated or unsaturated, aromatic or nonaromatic, ring optionally comprising at least one heteroatom and optionally fused with at least one saturated or unsaturated ring optionally comprising at least one heteroatom. In some embodiments, $R_1$ to $R_4$ jointly form from one to four rings.

In some embodiments, the disclosure relates to ortho-diphenol derivatives of formula (I), two adjacent substituents $R_1$-$R_2$, $R_2$-$R_3$ or $R_3$-$R_4$ of which cannot form a pyrrolyl radical with the carbon atoms which carry them. In some embodiments, $R_2$ and $R_3$ cannot form a pyrrolyl radical fused to the benzene ring carrying the two hydroxyls.

The saturated or unsaturated and optionally fused rings can also be optionally substituted.

The alkyl radicals can be saturated and linear or branched hydrocarbon radicals, for example, $C_1$-$C_{20}$ radicals, $C_1$-$C_{10}$ radicals, or $C_1$-$C_6$ alkyl radicals, such as methyl, ethyl, propyl, butyl, pentyl and hexyl.

The alkenyl radicals can be unsaturated and linear or branched $C_2$-$C_{20}$ hydrocarbon radicals, which in some embodiments comprise at least one double bond, such as ethylene, propylene, butylene, pentylene, 2-methylpropylene and decylene.

The aryl radicals can be mono- or polycyclic (which may or may not be fused) carbon-comprising radicals, which in some embodiments comprise from 6 to 30 carbon atoms and have at least one ring which is aromatic; a phenyl, biphenyl, naphthyl, indenyl, anthracenyl and tetrahydronaphthyl is in some embodiments chosen as the aryl radical.

The alkoxy radicals can be alkyl-oxy radicals with the alkyl as defined above, for example, a $C_1$-$C_{10}$ alkyl, such as methoxy, ethoxy, propoxy or butoxy.

The alkoxyalkyl radicals can be $(C_1$-$C_{20})$alkoxy$(C_1$-$C_{20})$alkyl radicals, such as methoxymethyl, ethoxymethyl, methoxyethyl, ethoxyethyl, and the like.

The cycloalkyl radicals can be $C_4$-$C_8$ cycloalkyl radicals, for example, cyclopentyl and cyclohexyl radicals. The cycloalkyl radicals can be substituted cycloalkyl radicals, such as cycloalkyl radicals substituted by alkyl, alkoxy, carboxylic acid, hydroxyl, amine and/or ketone groups.

The alkyl or alkenyl radicals, when they are optionally substituted, can be substituted by at least one substituent carried by at least one carbon atom chosen from:
- a halogen atom;
- a hydroxyl group;
- a $C_1$-$C_2$ alkoxy radical;
- a $C_1$-$C_{10}$ alkoxycarbonyl radical;
- a (poly)hydroxy$(C_2$-$C_4)$alkoxy radical;
- an amino radical;
- a 5- or 6-membered heterocycloalkyl radical;
- an optionally cationic 5- or 6-membered heteroaryl radical, such as an imidazolium radical, which is optionally substituted by a $(C_1$-$C_4)$alkyl radical, for example, a methyl radical;
- an amino radical substituted by one or two identical or different $C_1$-$C_6$ alkyl radicals optionally carrying at least:
  - one hydroxyl group,
  - one amino group optionally substituted by one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other heteroatom other than or the same as nitrogen,
  - one quaternary ammonium group —$N^+R'R''R'''$ $M^-$ for which R', R'' and R''', which can be identical or different, represent a hydrogen atom or a $C_1$-$C_4$ alkyl group and $M^-$ represents the counterion of the corresponding organic acid, inorganic acid or halide,
  - or one optionally cationic 5- or 6-membered heteroaryl radical, such as an imidazolium radical, optionally substituted by a $(C_1$-$C_4)$alkyl radical, for example, a methyl radical;
- an acylamino (—NR—COR') radical in which the R radical can be a hydrogen atom or a $C_1$-$C_4$ alkyl radical optionally carrying at least one hydroxyl group and the R' radical is a $C_1$-$C_2$ alkyl radical; a carbamoyl $((R)_2N$—CO—$)$ radical in which the R radicals, which can be identical or different, represent a hydrogen atom or a $C_1$-$C_4$ alkyl radical optionally carrying at least one hydroxyl group; an alkylsulfonylamino ($R'SO_2$—NR—) radical in which the R radical represents a hydrogen atom or a $C_1$-$C_4$ alkyl radical optionally carrying at least one hydroxyl group and the R' radical represents a $C_1$-$C_4$ alkyl radical or a phenyl radical; or an aminosulfonyl $((R)_2N$—$SO_2$—$)$ radical in which the R radicals, which can be identical or different, represent a hydrogen atom or a $C_1$-$C_4$ alkyl radical optionally carrying at least one hydroxyl group, a carboxyl radical in the acid form or salified form (e.g., salified with an alkali metal or a substituted or unsubstituted ammonium);

a cyano group;

a nitro group;

a carboxyl or glycosylcarbonyl group;

a phenylcarbonyloxy group optionally substituted by at least one hydroxyl group;

a glycosyloxy group; and a phenyl group optionally substituted by at least one hydroxyl group.

The aryl or heterocyclic radicals or the aryl or heterocyclic part of the radicals when they are optionally substituted can be substituted by at least one substituent carried by at least one carbon atom chosen from:

a $C_1$-$C_{10}$, such as a $C_1$-$C_8$, alkyl radical optionally substituted by at least one radical chosen from the following radicals: hydroxyl, $C_1$-$C_2$ alkoxy, (poly)hydroxy($C_2$-$C_4$)alkoxy, acylamino or amino substituted by two identical or different $C_1$-$C_4$ alkyl radicals, which two radicals optionally carry at least one hydroxyl group or are able to form, with the nitrogen atom to which they are attached, a saturated or unsaturated and optionally substituted 5- to 7-membered, e.g., 5- or 6-membered, heterocycle optionally comprising another heteroatom identical to or different from nitrogen;

a halogen atom;

a hydroxyl group;

a $C_1$-$C_2$ alkoxy radical;

a $C_1$-$C_{10}$ alkoxycarbonyl radical;

a (poly)hydroxy($C_2$-$C_4$)alkoxy radical;

an amino radical;

a 5- or 6-membered heterocycloalkyl radical;

an optionally cationic 5- or 6-membered heteroaryl radical, such as an imidazolium radical, which is optionally substituted by a ($C_1$-$C_4$)alkyl radical, for example, a methyl radical;

an amino radical substituted by one or two identical or different $C_1$-$C_6$ alkyl radicals optionally carrying at least:

one hydroxyl group, one amino group optionally substituted by one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other heteroatom other than or the same as nitrogen, one quaternary ammonium group —N⁺R'R"R'" M⁻ for which R', R" and R'", which can be identical or different, represent a hydrogen atom or a $C_1$-$C_4$ alkyl group and M⁻ represents the counterion of the corresponding organic acid, inorganic acid or halide, or one optionally cationic 5- or 6-membered heteroaryl radical, such as an imidazolium radical, optionally substituted by a ($C_1$-$C_4$)alkyl radical, for example, a methyl radical;

an acylamino (—NR—COR') radical in which the R radical is a hydrogen atom or a $C_1$-$C_4$ alkyl radical optionally carrying at least one hydroxyl group and the R' radical is a $C_1$-$C_2$ alkyl radical; a carbamoyl ((R)$_2$N—CO—) radical in which the R radicals, which can be identical or different, represent a hydrogen atom or a $C_1$-$C_4$ alkyl radical optionally carrying at least one hydroxyl group;

an alkylsulfonylamino (R'SO$_2$—NR—) radical in which the R radical represents a hydrogen atom or a $C_1$-$C_4$ alkyl radical optionally carrying at least one hydroxyl group and the R' radical represents a $C_1$-$C_4$ alkyl radical or a phenyl radical; or an aminosulfonyl ((R)$_2$N—SO$_2$—) radical in which the R radicals, which can be identical or different, represent a hydrogen atom or a $C_1$-$C_4$ alkyl radical optionally carrying at least one hydroxyl group, a carboxyl radical in the acid form or salified form (e.g., salified with an alkali metal or a substituted or unsubstituted ammonium);

a cyano group;

a nitro group;

a polyhaloalkyl group, such as trifluoromethyl;

a carboxyl or glycosylcarbonyl group;

a phenylcarbonyloxy group optionally substituted by at least one hydroxyl group;

a glycosyloxy group; and a phenyl group optionally substituted by at least one hydroxyl group.

A "glycosyl radical" is understood to mean a radical resulting from a mono- or polysaccharide.

The radicals comprising at least one silicon atom can in some embodiments be polydimethylsiloxane, polydiphenylsiloxane, polydimethylphenylsiloxane or stearoxy dimethicone radicals.

The heterocyclic radicals can be, for example, radicals comprising, in at least one ring, at least one heteroatom chosen from O, N and S, for example, O or N, which are optionally substituted by a group or groups such as alkyl, alkoxy, carboxylic acid, hydroxyl, amine or ketone groups. These rings can comprise at least one oxo group on the carbon atoms of the heterocycle.

Mention may be made, among the heterocyclic radicals which can be used, of the furyl, pyranyl, pyrrolyl, imidazolyl, pyrazolyl, pyridyl or thienyl groups.

In some embodiments, the heterocyclic groups can be fused groups, such as benzofuranyl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, e.g., by at least one OH group.

The ortho-diphenols of use in the method of the disclosure can be natural or synthetic. The natural ortho-diphenols include the compounds which can be present in nature and which can be reproduced by chemical (semi)synthesis.

The salts of the ortho-diphenols of the disclosure can be salts of acids or of bases. The acids can be inorganic or organic acids. In some embodiments, the acid is hydrochloric acid, which results in the chlorides.

The bases can be inorganic or organic bases. In some embodiments, the bases can be alkali metal hydroxides, such as sodium hydroxide, which results in sodium salts.

In some embodiments, the composition comprises, as ingredient i), at least one synthetic ortho-diphenol derivative which does not exist in nature.

In some embodiments, the method for dyeing keratinous fibers employs, as ingredient i), at least one natural ortho-diphenol derivative.

In some embodiments, the at least one ortho-diphenol derivative used in the methods of the disclosure according to i) is chosen from:

flavanols, such as catechin and epicatechin gallate, flavonols, such as quercetin, anthocyanidins, such as cyanidin, delphinidin or petunidin, anthocyanins or anthocyans, such as myrtillin, orthohydroxybenzoates, for example gallic acid salts, flavones, such as luteolin, hydroxystilbenes, for example 3,3',4,5'-tetrahydroxystilbene, optionally oxylated (for example glucosylated),
3,4-dihydroxyphenylalanine and its derivatives,
2,3-dihydroxyphenylalanine and its derivatives,
4,5-dihydroxyphenylalanine and its derivatives,
dihydroxycinnamates, such as caffeic acid and chlorogenic acid,
orthopolyhydroxycoumarins,
orthopolyhydroxyisocoumarins,
orthopolyhydroxycoumarones,
orthopolyhydroxyisocoumarones,
orthopolyhydroxychalcones,
orthopolyhydroxychromones,
orthopolyhydroxyquinones,
orthopolyhydroxyxanthones,
1,2-dihydroxybenzene and its derivatives,
1,2,4-trihydroxybenzene and its derivatives,
1,2,3-trihydroxybenzene and its derivatives,
2,4,5-trihydroxytoluene and its derivatives,
proanthocyanidins, such as proanthocyanidins A1, A2, B1, B2, 3 and C1,
proanthocyanins,
tannic acid,
ellagic acid.

When a dyeing precursors exhibits D and L form, either form can be used in the compositions according to the disclosure, as well as the racemate.

In some embodiments, the natural ortho-diphenols result from extracts of animals, bacteria, fungi, algae and plants used in their entirety or partially. Regarding plants, the extracts can result from plants or plant parts such as fruits, including citrus fruits, vegetables, trees or bushes. Use may also be made of mixtures of these extracts, rich in ortho-diphenols, as defined above.

In some embodiments, the natural ortho-diphenol or ortho-diphenols of the disclosure result from extracts of plants or of plant parts.

Within the meaning of the disclosure, such an extract will be considered a compound i) if it is known to comprise an entity chosen from ortho-diphenol and derivatives thereof.

The extracts can be obtained by extraction of various parts of plants, such as, for example, the root, wood, bark, leaf, flower, fruit, pip, husk or peel.

Mention may be made, among extracts of plants, of extracts of tea leaves or of rose.

Mention may be made, among extracts of fruits, of extracts of apple or of grape (including grape seeds) or extracts of cocoa beans and/or pods.

Mention may be made, among extracts of vegetables, of extracts of potato or of onion skins.

Mention may be made, among extracts of tree wood, of extracts of pine bark or extracts of logwood.

Use may also be made of mixtures of plant extracts.

In some embodiments, the ortho-diphenol derivative or derivatives can be natural extracts rich in ortho-diphenols. In some embodiments, the ortho-diphenol derivative or derivatives are solely natural extracts.

The natural extracts according to the disclosure can be provided in the form of powders or of liquids. In some embodiments, the extracts of the disclosure can be provided in the form of powders.

In some embodiments, the synthetic or natural ortho-diphenol or ortho-diphenol derivative(s) and/or the natural extract(s) used as ingredient i) in at least one composition of use in the methods according to the disclosure can be present in an amount ranging from 0.001% to 20% by weight of the total weight of the composition or compositions comprising the ortho-diphenol or ortho-diphenols or the extract or extracts.

As regards the pure ortho-diphenols, the content in the composition or compositions comprising them can range, for example, from 0.001% to 5% by weight of each of these compositions.

As regards the extracts, the content in the composition or compositions comprising extracts as is can range, for example, from 0.5% to 20% by weight of each of these compositions.

ii) Metal Salt

The methods of the disclosure use at least one ingredient ii) which is a metal salt.

In some embodiments, the metal salt is a salt of a divalent metal. In some embodiments, the metal salt is a salt of a transition metal. In some embodiments, the metal salt is not a salt of an alkali metal.

In some embodiments, the at least one metal salt is chosen from manganese (Mn) and zinc (Zn) salts.

Within the meaning of the present disclosure, "salt" is understood to include the oxides and hydroxides of these metals and the salts proper that can result from the action of an acid on a metal. In some embodiments, the at least one salt is not an oxide. In some embodiments, the at least one salt is not a hydroxide. Mention may be made, among the salts, of halides, such as chlorides, fluorides and iodides, sulfates, phosphates, nitrates, perchlorates and salts of carboxylic acids and polymeric complexes which can support said salts, and also their mixtures.

In some embodiments, the manganese salt is other than manganese carbonate, manganese hydrogencarbonate or manganese dihydrogencarbonate.

Mention may be made, as examples of polymeric complexes which can support said salts, of manganese pyrrolidonecarboxylate.

The salts of carboxylic acids which can be used in the disclosure also include salts of hydroxylated carboxylic acids, such as gluconate.

Mention may be made, as examples, of manganese chloride, manganese fluoride, manganese acetate tetrahydrate, manganese lactate trihydrate, manganese phosphate, manganese iodide, manganese nitrate trihydrate, manganese bromide, manganese perchlorate tetrahydrate, manganese sulfate monohydrate and manganese gluconate. In some embodiments, the at least one salt is chosen from manganese gluconate and manganese chloride. In some embodiments, the at least one salt comprises manganese gluconate and manganese chloride.

Mention may be made, among zinc salts, of zinc sulfate, zinc gluconate, zinc chloride, zinc lactate, zinc acetate, zinc glycinate and zinc aspartate.

The manganese and zinc salts can be introduced in the solid form into the compositions or else can originate from a natural, mineral or thermal, water rich in these ions or also from sea water (far example, Dead Sea water). They can also originate from inorganic compounds, such as earths or ocres, such as clays (for example green clay), or from plant extracts comprising them.

In some embodiments, the at least one metal salt of the disclosure has an oxidation state of 2, such as Mn(II) and Zn(II).

In some embodiments, the metal salt or salts used can be present in an amount ranging from 0.001% to 10% by weight of the total weight of the composition(s) comprising this or these metal salts, for example, from 0.05% to 0.1% by weight.

iii) Hydrogen Peroxide or System(s) which Generate(s) Hydrogen Peroxide

In the context of the present disclosure, the third constituent is hydrogen peroxide or at least one system which generate(s) hydrogen peroxide, such as:
  a) urea hydrogen peroxide;
  b) at least one polymeric complex which releases hydrogen peroxide, such as polyvinylpyrrolidone/$H_2O_2$, or other polymeric complexes such as those described in U.S. Pat. Nos. 5,008,093, 3,376,110, and 5,183,901 (in some embodiments, the at least one polymeric complex which releases hydrogen peroxide can be provided in the form of a powder);
  c) at least one oxidase which produces hydrogen peroxide in the presence of an appropriate substrate (for example, glucose in the case of glucose oxidase or uric acid with uricase);
  d) at least one metal peroxide which, in water, generates hydrogen peroxide, such as calcium peroxide or magnesium peroxide;
  e) at least one perborate; or
  f) at least one percarbonate.

In some embodiments, the composition or compositions comprise at least one system which generates hydrogen peroxide, chosen from a) urea hydrogen peroxide; b) at least one polymeric complex which releases hydrogen peroxide, such as polyvinylpyrrolidone/$H_2O_2$; c) at least one oxidase; d) at least one perborate; and e) at least one percarbonate.

In some embodiments, the third constituent is hydrogen peroxide.

Furthermore, the composition or compositions comprising the hydrogen peroxide or the least one system which generates hydrogen peroxide can also include at least one of various adjuvants used conventionally in compositions for dyeing the hair, which include those described herein.

In some embodiments, the hydrogen peroxide or the at least one system which generates hydrogen peroxide can be present in an amount ranging from 0.001% to 12% by weight of hydrogen peroxide, with respect to the total weight of the composition or compositions comprising it or them, and more for example, from 0.2% to 2.7% by weight.

In some embodiments, the at least one system which generates hydrogen peroxide does not comprise material that is effervescent as a solid. Materials that are effervescent as a solid include powders and pebbles that can produce bubbling, foaming or liberation of a gas, which can occur, for example, upon contact with a solvent or solution, such as a protic solvent, a solution at acidic pH, or a solution or solvent comprising a free Lewis acid.

iv) (bi)Carbonate(s)

In the context of the present disclosure, the fourth ingredient can be chosen from carbonates and bicarbonates.

Carbonates and bicarbonates (collectively, (bi)carbonates) include:
  a) carbonates of alkali metals ($Met^+_2CO_3^{2-}$), of alkaline earth metals ($Met'^{2+}CO_3^{2-}$), of ammonium (($R''_4N^+)_2CO_3^{2-}$) or of phosphonium (($R''_4P^+)_2CO_3^{2-}$), with Met' representing an alkaline earth metal and Met representing an alkali metal and R'', which can be identical or different, representing a hydrogen atom or an optionally substituted ($C_1$-$C_6$)alkyl group, such as a hydroxyethyl group, and
  b) bicarbonates, also known as hydrogencarbonates, with the following formulae:
    $R'^+HCO_3^-$, with R' representing a hydrogen atom, an alkali metal or an ammonium $R''_4N^+$ or phosphonium $R''_4P^+$ group, where R'', which can be identical or different, represent a hydrogen atom or an optionally substituted ($C_1$-$C_6$)alkyl group, such as a hydroxyethyl group, and, when R' represents a hydrogen atom, the hydrogencarbonate is then referred to as dihydrogencarbonate ($CO_2$, $H_2O$); and
    $Met'^{2+}(HCO_3^-)_2$, with Met' representing an alkaline earth metal.

In some embodiments, the fourth ingredient is chosen from alkali metal or alkaline earth metal (bi)carbonates, such as alkali metal (bi)carbonates.

Mention may be made of sodium, potassium, magnesium or calcium carbonates or hydrogencarbonates and their mixtures, such as sodium hydrogencarbonate. These hydrogencarbonates can originate from a natural water, for example spring water from the Vichy basin or from La Roche-Posay or Badoit. In some embodiments, the at least one (bi)carbonate is chosen from sodium carbonate [497-19-8]=$Na_2CO_3$, sodium hydrogencarbonate or sodium bicarbonate [144-55-8]=$NaHCO_3$, and calcium bicarbonate (also known as calcium dihydrogencarbonate)=$Na(HCO_3)_2$.

According to the disclosure, the (bi)carbonate agent or agents used can be present in an amount ranging from 0.001% to 10% by weight of the total weight of the composition or compositions comprising the (bi)carbonate agent or agents, for example, from 0.005% to 5% by weight.

v) Water:

In some embodiments, water is used in the method of the disclosure. It can be provided by wetting of the keratinous fibers and/or as part of the composition or compositions comprising the compounds i) to iv) as defined above, or from at least one other composition. In some embodiments, the water originates at least from a composition comprising at least one compound chosen from i) to iv) as defined above.

In some embodiments, at least one of the at least one ortho-diphenol derivative, the at least one metal salt, the hydrogen peroxide or at least one system which generates hydrogen peroxide, or the at least one (bi)carbonate is applied to keratinous fibers in a composition comprising water in an amount greater than or equal to 50%, 60%, 70%, 80%, 90%, 91%, 92%, 93%, 94%, 95%, 96%, 97%, or 98% by weight of the total weight of the composition. In some embodiments, at least one of the at least one ortho-diphenol derivative, the at least one metal salt, the hydrogen peroxide or at least one system which generates hydrogen peroxide, or the at least one (bi)carbonate is applied to keratinous fibers in a composition comprising water in an amount ranging from 50% to 98%; from 60% to 97%; from 70% to 96%; from 80% to 95%; from 90% to 95%; from 60% to 97%; from 70% to 96%; from 80% to 95%; or from 90% to 95%.

In some embodiments, the cosmetic compositions according to the disclosure comprise at least one ortho-diphenol derivative; at least one metal salt; hydrogen peroxide or at least one system which generates hydrogen peroxide; at least one (bi)carbonate, and water, wherein the water is present in an amount greater than or equal to 50%, 60%, 70%, 80%, 90%, 91%, 92%, 93%, 94%, 95%, 96%, 97%, or 98% by weight of the total weight of the cosmetic composition. In some embodiments, the cosmetic compositions according to the disclosure comprise at least one ortho-diphenol derivative; at least one metal salt; hydrogen peroxide or at least one system which generates hydrogen peroxide; at least one (bi) carbonate, and water, wherein the water is present in an amount ranging from 50% to 98%; from 60% to 97%; from 70% to 96%; from 80% to 95%; from 90% to 95%; from 60% to 97%; from 70% to 96%; from 80% to 95%; or from 90% to 95%.

In some embodiments, the multicompartment devices according to the disclosure comprise from 2 to 5 compartments comprising from 2 to 5 compositions which collectively comprise at least one ortho-diphenol derivative; at least one metal salt; hydrogen peroxide or at least one system which generates hydrogen peroxide; at least one (bi)carbonate; and water, said 2 to 5 compositions being aqueous or pulverulent, with at least one of these compositions being aqueous, wherein water is present in the 2 to 5 compositions in a total amount greater than or equal to 50%, 60%, 70%, 80%, 90%, 91%, 92%, 93%, 94%, 95%, 96%, 97%, or 98% by weight of the total weight of the 2 to 5 compositions.

In some embodiments, the multicompartment devices according to the disclosure comprise from 2 to 5 compartments comprising from 2 to 5 compositions which collectively comprise at least one ortho-diphenol derivative; at least one metal salt; hydrogen peroxide or at least one system which generates hydrogen peroxide; at least one (bi)carbonate; and water, said 2 to 5 compositions being aqueous or pulverulent, with at least one of these compositions being aqueous, wherein water is present in the 2 to 5 compositions in a total amount ranging from 50% to 98%; from 60% to 97%; from 70% to 96%; from 80% to 95%; from 90% to 95%; from 60% to 97%; from 70% to 96%; from 80% to 95%; or from 90% to 95%.

In some embodiments, said 2 to 5 compositions can be aqueous or pulverulent, with at least one of these compositions being aqueous, wherein water is present in the 2 to 5 compositions in a total amount greater than or equal to 50% by weight of the total weight of the 2 to 5 compositions.

vi) Cosmetic Compositions:

The cosmetic compositions according to the disclosure can comprise a cosmetically acceptable dyeing vehicle, such as a dyeing vehicle comprising water, a mixture of water and of at least one organic solvent, or at least one organic solvent.

The term "organic solvent" is understood to mean an organic substance capable of dissolving or dispersing another substance without modifying it chemically.

In some embodiments, the cosmetic dyeing compositions according to the disclosure comprise water.

In some embodiments, the cosmetic compositions according to the disclosure comprise i) at least one entity chosen from ortho-diphenol and derivatives thereof, ii) at least one metal salt, iii) hydrogen peroxide or at least one system which generates hydrogen peroxide, and iv) at least one (bi)carbonate, wherein the ingredients i) through iv) are mutually different, i.e., one entity or chemical species does not serve as two of the ingredients i) through iv).

The Organic Solvents:

Mention may be made, as organic solvents, for example, of lower $C_1$-$C_4$ alkanols, such as ethanol and isopropanol, polyols and polyol ethers, such as 2-butoxyethanol, propylene glycol, propylene glycol monomethyl ether, diethylene glycol monoethyl ether, diethylene glycol monomethyl ether or hexylene glycol, and aromatic alcohols, such as benzyl alcohol or phenoxyethanol.

The organic solvent(s) can be present in proportions ranging from 1% to 40% by weight, with respect to the total weight of the dyeing composition, or from 5% to 30% by weight.

The Adjuvants:

The composition or compositions of the coloring method in accordance with the disclosure can also include various adjuvants conventionally used in compositions for dyeing the hair, which can be chosen from anionic, cationic, nonionic, amphoteric or zwitterionic surface-active agents or their mixtures, anionic, cationic, nonionic, amphoteric or zwitterionic polymers or their blends, inorganic or organic thickening agents, such as anionic, cationic, nonionic and amphoteric polymeric associative thickeners, antioxidants, penetration agents, sequestering agents, fragrances, buffers, dispersing agents, conditioning agents, such as, for example, volatile or nonvolatile and modified or unmodified silicones, film-forming agents, ceramides, preservatives and opacifying agents.

Said adjuvants can be chosen from surface-active agents, such as anionic or nonionic surfactants or their mixtures, and inorganic or organic thickening agents.

The above adjuvant or adjuvants can be present in an amount, for each of them, ranging from 0.01% to 40% by weight, with respect to the weight of the composition, for example, from 0.1% to 20% by weight, with respect to the weight of the composition.

Of course, a person skilled in the art will take care to choose the optional additional compound or compounds so that the beneficial properties of the at least one composition of use in the coloring method in accordance with the disclosure are not, or not substantially, detrimentally affected by the envisaged addition or additions.

The Additional Dyes:

The method employing the ingredients i) to v) as defined above or the cosmetic composition according to the disclosure comprising the ingredients i) to v) as defined above can in addition employ or comprise at least one direct dye. These direct dyes can be, for example, chosen from those conventionally used in direct dyeing, among which may be mentioned any of the aromatic and/or nonaromatic dyes commonly used, such as neutral, acid or cationic nitrobenzene direct dyes, neutral, acid or cationic azo direct dyes, natural direct dyes other than ortho-diphenols, neutral, acid or cationic quinones such as anthraquinone direct dyes, azine, triarylmethane or indoamine direct dyes, methines, styryls, porphyrins, metalloporphyrins, phthalocyanines, methinecyanines and fluorescent dyes. All of these additional dyes are different from the entity chosen from ortho-diphenol and derivatives thereof according to the disclosure.

Mention may be made, among natural direct dyes, of lawsone, juglone, indigo, isatin, curcumin, spinulosin, apigenidine or orceins. Use may also be made of extracts or decoctions comprising these natural dyes such as cataplasms or henna-based extracts.

The additional direct dye or dyes used in the composition or the compositions can range from 0.001% to 10% by weight of the total weight of the composition(s) comprising them, for example, from 0.05% to 5% by weight.

The compositions of the method employing the ingredients i) to v) as defined above or the cosmetic composition according to the disclosure comprising the ingredients i) to v) as defined above can also employ or comprise at least one oxidation base and/or at least one coupler conventionally used for the dyeing of keratinous fibers.

Mention may be made, among the oxidation bases, of para-phenylenediamines, bisphenylalkylenediamines, para-aminophenols, bis-para-aminophenols, ortho-aminophenols, heterocyclic bases and their addition salts.

Mention may be made, among these couplers, of meta-phenylenediamines, meta-aminophenols, meta-diphenols, naphthalene couplers, heterocyclic couplers and their addition salts.

The oxidation base(s) present in the composition(s) can be present each in an amount ranging from 0.001% to 10% by weight of the total weight of the corresponding composition(s).

The cosmetic composition(s) of the disclosure can be provided in various formulation forms, such as a powder, a lotion, a foam, a cream or a gel, or in any other form appropriate for carrying out dyeing of keratinous fibers. It can also be packaged as a propellant-free pump-action spray or under pressure in an aerosol container in the presence of a propellant and form a foam.

pH of the Composition(s)

In some embodiments, the pH of the composition or compositions comprising the (bi)carbonate or (bi)carbonates is greater than 7; in some embodiments, said pH ranges from 8 to 12, e.g., from 8 to 10.

The pH of the composition or compositions comprising the hydrogen peroxide or a system which generates hydrogen peroxide can in some embodiments have a pH less than 7, e.g., a pH ranging from 1 to 5, such as if the composition or compositions do not comprise (bi)carbonates.

In some embodiments, the composition or compositions comprising the ortho-diphenol or ortho-diphenols of the disclosure and not comprising (bi)carbonates can be at a pH of less than 7, e.g., a pH ranging from 3 to 6.5.

According to a form of the disclosure, the compositions comprising the metal salt or salts and not comprising (bi)carbonates can be at a pH of less than 7, e.g., a pH ranging from 3 to 6.5.

The pH of these compositions can be adjusted to the desired value using an acidifying or basifying agent or agents commonly used in the dyeing of keratinous fibers and/or using a conventional buffer system or systems.

Mention may be made, among the acidifying agents of the compositions used in the disclosure, by way of example, of inorganic or organic acids, such as hydrochloric acid, ortho-phosphoric acid, sulfuric acid, carboxylic acids, such as acetic acid, tartaric acid, citric acid or lactic acid, or sulfonic acids.

In some embodiments, a basifying agent is added to at least one of the compositions of the dyeing method comprising the (bi)carbonate or (bi)carbonates. This basic agent can be chosen from aqueous ammonia, alkali metal carbonates, alkanolamines such as mono- di- and triethanolamines and also their derivatives, sodium or potassium hydroxides and the compounds of formula (II):

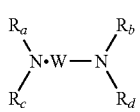

(II)

in which W is a propylene residue optionally substituted by a hydroxyl group or a $C_1$-$C_4$ alkyl radical and $R_a$, $R_b$, $R_c$ and $R_d$, which can be identical or different, represent a hydrogen atom, a $C_1$-$C_4$ alkyl radical or a $C_1$-$C_4$ hydroxyalkyl radical.

vii) Single- Or Multistage Coloring Method

In some embodiments, the dyeing method is carried out in at least one stage, by application to the keratinous fibers of at least one cosmetic composition comprising, taken together or separately, in said at least one composition, the following ingredients:

i) at least one entity chosen from ortho-diphenol and derivatives thereof;
 ii) at least one metal salt, such as Mn and Zn salts;
 iii) hydrogen peroxide or at least one system which generates hydrogen peroxide; and
 iv) at least one (bi)carbonate or at least one system which generates at least one (bi)carbonate,
 it being understood that at least one of said compositions is aqueous, and with the proviso that if the at least one system which generates hydrogen peroxide is used, then the at least one (bi)carbonate and the at least one metal salt are applied in separate stages. This is to say, according to the disclosure, the above ingredients i)-iv) can be added in one stage or in multiple stages. They can be added in the form of one composition that comprises each of ingredients i)-iv), or they can be added in the form of at least two compositions that collectively comprise each of ingredients i)-iv).

In some embodiments, there is a leave-in time between the stages of application of the compositions comprising the ingredient or ingredients i), ii), iii) and/or iv). In some embodiments, the leave-in time ranges from 3 to 120 minutes, such as from 10 to 60 minutes or from 15 to 45 minutes.

The keratinous fibers may or may not be pre-wetted.

In some embodiments, the compound or compound(s) iv) can be applied to the keratinous fibers:

in a mixture with the ingredients i), ii) and iii);
 separately, after application of a cosmetic composition comprising the ingredients i), ii) and iii); or
 together with the ingredient iii) after application of a cosmetic composition comprising the ingredients i) and ii).

In some embodiments, the methods are single- or two-stage coloring methods.

In some embodiments, the method for coloring keratinous fibers is carried out in a single stage by the application, to the keratinous fibers, of an aqueous cosmetic dye composition comprising i), ii), iii) and iv) as defined above.

The leave-in time after application is in some embodiments a time ranging from 3 to 120 minutes, such as from 10 to 60 minutes or from 15 to 45 minutes.

In some embodiments, the method for coloring keratinous fibers is carried out in two stages.

In some embodiments of the two-stage method, the first stage consists of applying, to said fibers, a cosmetic composition comprising the ingredients i), ii) and iii) as defined herein and then, a second stage comprises applying a cosmetic composition comprising the ingredients iv) as defined herein to said fibers, it being understood that at least one of the two compositions is aqueous.

In some embodiments of the method for coloring keratinous fibers in two stages, the first stage consists of applying, to said fibers, a composition comprising the ingredients i) and ii) as defined above and then, a second stage comprises applying a second cosmetic composition comprising the ingredients iii) and iv) as defined above to said fibers. In some embodiments, at least one of the two compositions is aqueous.

In some embodiments, the method for coloring keratinous fibers is carried out in at least two stages ending by a keratin fibers treatment with the ingredient iv) and can be followed by post-treatment stages such as a shampooing stage with the aid of classic shampooing, a rinse stage such as with water, and/or a keratin fibers drying stage by a heat treatment such as defined herein; provided that said process does not comprise an intermediate rinse stage just before the step which carries out ingredient iv).

In some embodiments, the method for coloring keratinous fibers is carried out in two stages: in the first stage the ingredients i) and ii) can be together applied on keratin fibers the then in a second stage the ingredients iii) and iv) can be applied on keratinous fibers or in the first stage ingredients the ingredients i), ii) and iii) can be together applied on keratinous fibers then in a second stage the ingredient iv) can be applied on keratinous fibers. These processes can be followed by a post-treatment comprising at least one stages such as a rinse stage such as with water, and/or a shampooing stage with the aid of classic shampooing, and/or a keratinous fibers drying stage by heat treatment such as defined hereinafter. In some embodiments, the method for coloring keratinous fibers in at least 2 stages is not carried out with an intermediate rinse stage between the first and second stages, i.e. between the treatment of keratinous fibers with the mixture of ingredients i), ii), and iii) and the treatment of keratinous fibers with ingredient iv), or between the treatment of keratinous fibers with the mixture of ingredients i), ii) and the treatment of keratinous fibers with the mixture of iii) and iv).

In some embodiments, the methods according to the disclosure comprise, just before applying the at least one (bi) carbonate to the keratinous fibers at least one of:
a) mechanically wiping the keratinous fibers, such as defined herein; and
b) drying the keratinous fibers by heating treatment, such as defined herein.

In some embodiments, the keratinous fibers are unrinsed, i.e., the above mechanical wiping and drying are successively carried out without an intervening rinsing.

The methods according to the disclosure comprise, in some embodiments, between the first and second stages discussed above:
a) mechanically wiping the keratinous fibers, such as defined herein; and
b) drying the keratinous fibers by heating treatment, such as defined herein.

In some embodiments, the keratinous fibers are unrinsed, i.e., the above mechanical wiping and drying are successively carried out without an intervening rinsing.

In some embodiments, the mechanical wiping is performed with an absorbent item as the wiper, e.g., a piece of cloth, such as a towel, for example, a terry towel, a dish towel, a paper towel or other absorbent paper. In some embodiments, keratinous fibers are dried by heating with heat treatment at a temperature ranging from 60 to 220° C., such as from 120 to 200° C.

In some embodiments, the method for coloring keratinous fibers in at least 2 stages is carried out with an intermediate very fast rinse stage between the first and second stages, i.e., between the treatments of keratinous fibers with the mixture of ingredients i), ii), iii) and with ingredient iv), or between the treatments of keratinous fibers with the mixture of ingredients i), ii) and with the mixture of ingredients iii) and iv). The period of rinse stage length can range from 1 second to 1 minute, from 1 second to 30 seconds, or from 2 to 5 seconds, such as 2 seconds; tap water or tap shower water can be used, such as with a strong water jet. The latter fast rinse stage can be followed by a mechanical wiping such as defined hereinafter.

In some of these embodiments, the leave-in time after application of the cosmetic composition for the first stage can be a time ranging from 3 to 120 minutes, such as from 10 to 60 minutes or from 15 to 45 minutes. The leave-in time after application of the second cosmetic composition for the second stage can be a time ranging from 3 to 120 minutes, such as from 3 to 60 minutes or from 5 to 30 minutes.

Whatever the method of application, the application temperature can range from ambient temperature (ambient temperature ranging from about 15 to about 25° C.) to 80° C., such as from 15 to 45° C. Thus, in some embodiments, after application of the composition or compositions according to the disclosure, the hair can be subjected to a heat treatment by heating at a temperature ranging from 30 to 60° C. In practice, this operation can be carried out using a hair styling hood, a hair dryer, a dispenser of infrared rays, or any other conventional heating device.

Use may be made, both as a device for heating and for smoothing the hair, of a heating iron at a temperature ranging from 60 to 220° C., such as from 120 to 200° C.

A form of the disclosure relates to a coloring method which is carried out at ambient temperature (25° C.).

In all the embodiments described above, it is possible for the compositions mentioned to be ready-for-use compositions such as result from the mixing, at the time of use, of at least two compositions, which can be compositions provided in a dyeing kit or kits.

Stage(s) of Mechanical Wiping and/or of Drying:

The methods for dyeing keratinous fibers according to the disclosure comprise at least one intermediate stage of mechanical wiping of the fibers and/or of drying.

The mechanical wiping and drying stages are also called "controlled leave-in" stages, which differ from a "rinse-out" stage performed under an intense water jet, and from a "non rinsing" or "leave in" procedure, in which there is immediate progression from the first to the second stage of development.

Mechanical wiping of the fibers is understood to mean the rubbing of an absorbent item over the fibers and the physical withdrawal, via the absorbent item, of the surplus of ingredient(s) which has/have not penetrated into the fibers. The absorbent item can be a piece of cloth, such as a towel, e.g., a terry towel, a dish towel, or paper towel or other absorbent paper.

In some embodiments, the mechanical wiping is performed in a way that leaves the keratinous fibers wet, i.e., the wiping does not cause total drying of the keratinous fibers. Drying is understood to mean the action of evaporating the organic solvents and/or water occurring in one or more compositions used in the methods of the disclosure, comprising or not comprising one or more ingredients i) to iv) as defined above. Drying can be carried out via a heat source (convection, conduction or radiation) by sending, for example, a hot gas stream, such as air, which promotes the evaporation of the solvent or solvents. Mention may be made, as heat source, of a hair dryer, including hood hair dryers, an iron for smoothing the hair, a dispenser of infrared rays, and any other conventional heating device.

Dyeing Device or "Kit":

Another subject matter of the disclosure is a dyeing "kit" or multicompartment device. This kit can comprise from 2 to 5 compartments comprising from 2 to 5 compositions in which the ingredients i) at least one entity chosen from ortho-diphenol and derivatives thereof, ii) at least one metal salt, iii) hydrogen peroxide or at least one system which generates hydrogen peroxide and iv) at least one (bi)carbonate, said compositions being aqueous or pulverulent. In some embodiments, at least one of these compositions is aqueous.

According to a first alternative form, the kit comprises five compartments, the first four compartments respectively comprising the ingredients, as powders, i), ii), iii) and iv) as defined above and the fifth compartment containing an aqueous composition, such as water. In this case, the compound or compounds iii) are hydrogen peroxide precursors.

Another alternative form relates to a kit comprising four compartments comprising an ingredient i) to iv) as defined above, wherein at least one of the ingredients is comprised by an aqueous composition contained in a compartment.

In another alternative form, the device comprises four compartments: the first compartment comprising a cosmetic composition comprising i) at least one entity chosen from ortho-diphenol and derivatives thereof, the second compartment comprising a composition comprising ii) at least one metal salt, the third compartment comprising a composition comprising iii) hydrogen peroxide or at least one system which generates hydrogen peroxide and the fourth compartment comprising a composition comprising iv) at least one (bi)carbonate; in some embodiments, at least one of these compositions is aqueous.

Another embodiment relates to a device comprising three compartments:

(a) a first compartment comprising a composition including:
  i) at least one entity chosen from ortho-diphenol and derivatives thereof; and
(b) a second compartment comprising a composition including:
  ii) at least one metal salt;
  iii) hydrogen peroxide or at least one system which generates hydrogen peroxide; and
(c) a third compartment comprising iv) at least one (bi)carbonate.

At least one of the three compositions can be aqueous, and the ortho-diphenol or ortho-diphenols can be in the powder form.

It is also possible to have a kit comprising three compartments, the first a) comprising a composition comprising i) at least one entity chosen from ortho-diphenol and derivatives thereof and ii) at least one metal salt, the second b) comprising a composition comprising iii) hydrogen peroxide or at least one system which generates hydrogen peroxide and the third c) comprising a composition comprising iv) at least one (bi)carbonate. In such a kit, at least one of the compositions can be aqueous; this composition can comprise hydrogen peroxide.

According to a form of the disclosure, the kit comprises two compartments: a first compartment comprising a composition comprising i) at least one entity chosen from ortho-diphenol and derivatives thereof, ii) at least one metal salt and iii) hydrogen peroxide or at least one system which generates hydrogen peroxide and a second compartment comprising iv) at least one (bi)carbonate.

The kits comprising two compartments may also include kits which comprise, in a first compartment, a composition comprising the compounds i), ii) and iv) as defined above and, in a second compartment, a composition comprising the compound iii) as defined above.

In these two alternative forms of the kit comprising two compartments, the first composition present in the first compartment comprising either i), ii) and iii) or i), ii) and iv) can be in the powder form, and the second composition can be aqueous.

According to an alternative form, the device according to the disclosure furthermore comprises an additional composition (c) comprising at least one treating agent.

The compositions of the device according to the disclosure can be packaged in separate compartments optionally accompanied by appropriate applicator which can be identical or different, such as brushes, including fine brushes, or sponges.

The device mentioned above can also be equipped with an instrument which facilitates delivery of the desired mixture to the hair, for example such as the devices described in patent FR 2 586 913.

By way of non-limiting illustration, concrete examples of certain embodiments of the present disclosure are given below. The examples that follow serve to illustrate the invention without, however, being limiting in nature.

DYEING EXAMPLES

Example 1

The following compositions were prepared:

| Composition | (a1) |
| --- | --- |
| Epicatechin | 10 g |
| Ethanol | 29 g |
| Propylene glycol | 29 g |
| Manganese chloride | 0.05 g |
| Hydroxypropyl cellulose | 0.5 g |
| Hydrogen peroxide | 1.2 g |
| Demineralized water | q.s. for 100 g |

| Composition | (b1) |
| --- | --- |
| Sodium bicarbonate | 2.6 g |
| Carbomer | 1 g |
| Monoethanolamine | q.s. for pH 9 |
| Demineralized water | q.s. for 100 g |

The composition (a1) was applied to dry natural hair comprising 90% white hairs with a bath ratio of 5 g of formulation per 1 g of hair. The treated hair was subsequently left to develop for 30 minutes using a drying hood at 45° C.

The composition (b1) was subsequently applied to hair for a development time of 10 minutes at ambient temperature. After a few minutes a very intense coppery red coloration appeared.

After being rinsed, shampooed and dried, the hair samples were dyed in an intense coppery shade. The coloring was very persistent with regard to washing operations and light.

Example 2

The following compositions were prepared:

| Compositions | (a2) |
| --- | --- |
| Extract of green tea leaves | 5 g |
| Sodium lauryl ether sulfate at 70% in water | 10 g |
| Hexylene glycol | 5 g |
| Manganese gluconate | 0.05 g |
| Hydrogen peroxide | 1.2 g |
| Demineralized water | q.s. for 100 g |

| Composition | (b1) |
|---|---|
| Sodium bicarbonate | 2.6 g |
| Carbomer | 1 g |
| Monoethanolamine | q.s. for pH 9 |
| Demineralized water | q.s. for 100 g |

The composition (a2) was applied to dry natural hair comprising 90% white hairs with a bath ratio of 5 g of formulation per 1 g of hair. The treated hair was subsequently left to develop at ambient temperature for 45 minutes.

The composition (b1) was subsequently applied to hair for a development time of 10 minutes at ambient temperature.

After having rinsed, shampooed and dried, the hair samples are respectively dyed in a natural light golden shade. The coloring was very persistent with regard to washing operations and light.

I) Comparative Examples

The following compositions were prepared:

| Composition A | A1 comparative | A2 comparative | A3 disclosure | A4 disclosure | A5 disclosure |
|---|---|---|---|---|---|
| Catechin | 5 g | — | 5 g | — | — |
| Cocoa bean extract | — | — | — | 5 g | — |
| Pine bark extract | — | 5 g | — | — | 5 g |
| Hexylene glycol | 5 g | 5 g | 5 g | 5 g | 5 g |
| Sodium lauryl ether sulfate (70% as AM) | 3.75 g | 3.75 g | 3.75 g | 3.75 g | 3.75 g |
| Manganese chloride tetrahydrate (i.e. 0.01% by weight of Mn2+ metal equivalent) | 0.036 g | 0.036 g | 0.036 g | — | 0.036 g |
| Manganese pyrrolidone carboxylate (i.e. 0.006% by weight of Mn2+ metal equivalent) | — | — | — | 0.062 g | — |
| Hydrogen peroxide | — | — | 1.2 g | 1.2 g | — |
| 35% urea hydrogen peroxide (i.e. 1.2% by weight of hydrogen peroxide equivalent) | — | — | — | — | 3.4 g |
| Citric acid or sodium hydroxide | q.s. for pH 5 | q.s. for pH 5 | q.s. for pH 5 | q.s. for pH 5 | q.s. for pH 5 |
| Demineralized water | q.s. for 100 g | q.s. for 100 g | q.s. for 100 g | q.s. for 100 g | q.s. for 100 g |

The composition A was applied to locks of dry natural hair comprising 90% white hairs and to dry permed hair comprising 90% white hairs with a bath ratio of 5 g of formulation per 1 g of hair. The treated hair was subsequently left to develop at a temperature of 50° C. for 30 minutes.

At the end, the hair impregnated with the first composition was wiped using an absorbent paper towel in order to remove the excess formulation.

| Composition B | B1 |
|---|---|
| Sodium bicarbonate: NaHCO$_3$ | 2.6 g |
| Carbomer | 1 g |
| Monoethanolamine | q.s. for pH 9 |
| Demineralized water | q.s. for 100 g |

The composition B was subsequently applied to the hair with a bath ratio of 4 g per 1 g of lock; the development time was 10 minutes at ambient temperature. After a few minutes, a very intense coloring appeared. The hair was subsequently rinsed with water, washed with a conventional shampoo and dried under a hood.

Colorimetric Results:

The coloring of the hair was evaluated visually and read on a Minolta spectrocolorimeter (CM3600d, illuminant D65, angle 10°, SCI values) for the L*, a*, b* colorimetric measurements.

In this L*, a*, b* system, L* represents the intensity of the color, a* indicates the green/red color axis and b* indicates the blue/yellow color axis. The lower the value of L, the darker or more intense the color. The higher the value of a*, the redder the shade; the higher the value of b*, the yellower the shade.

The variation in coloring between the colored locks of natural/permed white hair which was untreated (control) and after treatment are defined by ΔE* according to the following equation:

$$\Delta E^* = \sqrt{(L^*-L_o^*)^2+(a^*-a_o^*)^2+(b^*-b_o^*)^2}$$

In this equation, L*, a* and b* represent the values measured after dyeing the natural/permed hair comprising 90% white hairs and $L_o^*$, $a_o^*$ and $b_o^*$ represent the values measured for the untreated natural/permed hair comprising 90% white hairs.

The greater the value of ΔE, the greater the difference in color between the control locks and the dyed locks.

The coloring was very persistent toward washing operations and light.

|  | Examples (on natural hair comprising 90% white hairs) | | | | | |
| --- | --- | --- | --- | --- | --- | --- |
|  | Control (untreated hair) | 3 | 4 | 5 | 6 | 7 |
| Composition (Ai) Stage 1 | — | A1 | A2 | A3 | A4 | A5 |
| Composition (Bi) Stage 2 | — | B1 | B1 | B1 | B1 | B1 |
| Shades on hair | — | very light golden | very light beige | very intense coppery | very intense coppery | golden coppery |
| Intensity (L*) | 47.08 | 51.08 | 46.28 | 41.32 | 45.22 | 47.93 |
| a* | 1.9 | 3.31 | 3.48 | 11.2 | 8.94 | 7.54 |
| b* | 11.74 | 20.31 | 13.66 | 25.77 | 22.71 | 18.42 |
| ΔE* | — | 9.56 | 2.62 | 17.79 | 13.17 | 8.79 |
| ΔL* | — | 4 | −0.8 | −5.76 | −1.85 | 0.86 |
| Δa* | — | 1.41 | 1.59 | 9.3 | 7.04 | 5.64 |
| Δb* | — | 8.57 | 1.93 | 14.03 | 10.98 | 6.68 |
|  | Examples (on natural hair comprising 90% white hairs) | | | | | |
|  | Control (untreated hair) | 8 | 9 | 10 | 11 | 12 |
| Composition (Ai) Stage 1 | — | A1 | A2 | A3 | A4 | A5 |
| Composition (Bi) Stage 2 | — | B1 | B1 | B1 | B1 | B1 |
| Shades on hair | — | very light golden | very light beige | very intense coppery | very intense coppery | golden coppery |
| L* | 47.22 | 45.48 | 47.63 | 41.58 | 38.64 | 47.3 |
| a* | 0.31 | −0.06 | 1.16 | 9 | 10.39 | 6.58 |
| b* | 0.45 | 15.54 | 12.6 | 26.42 | 25.08 | 17.39 |
| ΔE* | — | 5.4 | 2.35 | 19.04 | 19.73 | 9.36 |
| ΔL* | — | −1.74 | −0.41 | −5.63 | −8.58 | 0.09 |
| Δa* | — | −0.37 | 0.85 | 8.69 | 10.08 | 6.27 |
| Δb* | — | 5.09 | 2.15 | 15.97 | 14.64 | 6.95 |

It is apparent from the above tables that the locks of natural or permed white hair treated with the composition according to the disclosure made it possible to dye in a significantly more chromatic way than the composition according to the comparison test (see A1+B1 vs A3+B1; and A2+B1 vs A4+B1 and A5+B1). Furthermore, the compositions according to the disclosure provided the hair with a much more intense color than those obtained with the comparison tests (L* lower with the compositions according to the disclosure).

II) Other Comparative Examples

The following compositions were prepared:

| Composition A' | A'1 Disclosure | A'2 Comparative | A'3 Disclosure | A'4 Comparative |
| --- | --- | --- | --- | --- |
| Catechin | 4 g | 4 g | 4 g | 4 g |
| Hexylene glycol | 5 g | 5 g | 5 g | 5 g |
| Sodium lauryl ether sulfate (70% as AM) | 3.75 g | 3.75 g | 3.75 g | 3.75 g |
| Manganese chloride tetrahydrate (i.e. 0.01% by weight of $Mn^{2+}$ metal equivalent) | 0.036 g | — | 0.036 g | — |
| Hydrogen peroxide | 1.2 g | 1.2 g | — | — |
| Citric acid or sodium hydroxide | qsp pH 5 | qsp pH 5 | qsp pH 5 | qsp pH 5 |
| Demineralized water | qsp 100 g | qsp 100 g | qsp 100 g | qsp 100 g |

The composition A' was applied to locks of dry natural hair comprising 90% white hairs and to locks of dry permed hair comprising 90% white hairs with a bath ratio of 5 g of formulation per 1 g of hair. The treated hair was subsequently left to develop at a temperature of 50° C. for 30 minutes.

At the end, the hair impregnated with the first composition was wiped using an absorbent paper towel in order to remove the excess formulation.

| Composition B' | B'1 | B'2 | B'3 | B'4 |
|---|---|---|---|---|
| Sodium bicarbonate: NaHCO₃ | 2.6 g | 2.6 g | 2.6 g | 2.6 g |
| Manganese chloride tetrahydrate (i.e. 0.01% by weight of Mn²⁺ metal equivalent) | — | 0.036 g | — | 0.036 g |
| Hydrogen peroxide | — | — | 1.2 g | 1.2 g |
| Citric acid or sodium hydroxide | qsp pH 9 | qsp pH 9 | qsp pH 9 | qsp pH 9 |
| Demineralized water | qsp 100 g | qsp 100 g | qsp 100 g | qsp 100 g |

The composition B' was subsequently applied to the hair with a bath ratio of 4 g per 1 g of lock; the development time was 10 minutes at ambient temperature. After a few minutes, a very intense coloring appeared. The hair was subsequently rinsed with water, washed with a conventional shampoo and dried under a hood.

Colorimetric Results:

The coloring of the hair was evaluated visually and read on a Minolta spectrocolorimeter (CM3600d, illuminant D65, angle 10°, SCI values) for the L*, a*, b* colorimetric measurements.

Chromaticity: C*

Chromaticity in the CIE L*, a*, b* colorimetric system is calculated according to the following equation:

$$C^* = \sqrt{a^{*2} + b^{*2}}$$

The greater the value of C*, the greater the chromaticity is.

| | Examples (on natural hair comprising 90% of white hairs) | | | |
|---|---|---|---|---|
| | 13 | 14 | 15 | 16 |
| Composition (A'i) Stage 1 | A'1 | A'2 | A'3 | A'4 |
| Intermediate stage | | Non rinsed, wiped | | |
| Composition (B'i) stage 2 | B'1 | B'2 | B'3 | B'4 |
| Shades on hair | coppery | very light beige | Golden green | very light beige |
| Chromaticity (C*) | 34.30 | 17.66 | 30.71 | 20.63 |
| Intensity (L*) | 50.69 | 58.65 | 46.87 | 58.54 |

| | Examples (on natural hair comprising 90% of white hair) | | | |
|---|---|---|---|---|
| | 17 | 18 | 19 | 20 |
| Composition (A'i) Stage 1 | A'1 | A'2 | A'3 | A'4 |
| Intermediate stage | | Rinsed, wiped | | |
| Composition (B'i) stage 2 | B'1 | B'2 | B'3 | B'4 |
| Shades on hair | Golden green | very light beige | Golden green | very light beige |
| Chromaticity (C*) | 30.18 | 16.97 | 33.39 | 19.50 |
| Intensity (L*) | 45.07 | 57.83 | 45.82 | 62.04 |

It is apparent from the above tables that the locks of natural or permed white hair treated with the composition according to the disclosure made it possible to dye in a significantly more chromatic way than the composition according to the comparison test (see A'1+B'1 vs. A'2+B'2; and A'3+B'3 vs. A'4+B'4). Furthermore, the compositions according to the disclosure provided the hair with a much more intense color than those obtained with the comparison tests (L* lower with the compositions according to the disclosure).

What is claimed is:

1. A method for dyeing keratinous fibers, comprising treating said fibers with:
   i) at least one entity chosen from ortho-diphenol and derivatives thereof,
   ii) at least one metal salt,
   iii) hydrogen peroxide or at least one system which generates hydrogen peroxide, and
   iv) at least one (bi)carbonate,
   with the proviso that if the at least one system which generates hydrogen peroxide is used, the at least one (bi)carbonate and the at least one metal salt are applied in separate stages.

2. The dyeing method of claim 1, wherein the at least one entity chosen from ortho-diphenol and derivatives thereof is chosen from natural ortho-diphenol derivatives.

3. The dyeing method of claim 1, wherein the at least one entity is chosen from ortho-diphenol and derivatives thereof that comprise an aromatic ring chosen from benzene, naphthalene, tetrahydronaphthalene, indane, indene, anthracene, phenanthrene, isoindole, indoline, isoindoline, benzofuran, dihydrobenzofuran, chromane, isochromane, chromene, isochromene, quinoline, tetrahydroquinoline and isoquinoline, said aromatic ring comprising at least two hydroxyl groups carried by two contiguous adjacent atoms of the aromatic ring.

4. The dyeing method of claim 1, wherein the at least one entity chosen from ortho-diphenol and derivatives thereof is chosen from entities of formula (I) and their oligomers and salified forms thereof:

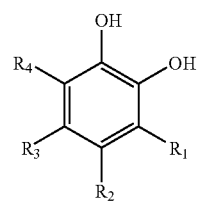

(I)

in which formula (I):
R₁ to R₄, which are identical or different, represent substituents chosen from:
   a hydrogen atom,
   a halogen atom,
   a hydroxyl radical,
   a carboxyl radical,
   an alkyl carboxylate or alkoxycarbonyl radical,
   an optionally substituted amino radical,
   an optionally substituted linear or branched alkyl radical,
   an optionally substituted linear or branched alkenyl radical,
   an optionally substituted cycloalkyl radical, an alkoxy radical,
an alkoxyalkyl radical,
an alkoxyaryl radical, it being possible for the aryl group to be optionally substituted,
an aryl radical,
a substituted aryl radical,
a saturated or unsaturated heterocyclic radical which does or does not carry a cationic or anionic charge, which is optionally substituted and/or which is optionally fused with an aromatic ring, said aromatic ring being optionally substituted, and
a radical comprising at least one silicon atom;
except that, two of the adjacent substituents $R_1$-$R_2$, $R_2$-$R_3$ or $R_3$-$R_4$ optionally instead jointly form a saturated or unsaturated, aromatic or nonaromatic and substituted or unsubstituted ring optionally comprising at least one heteroatom and optionally fused with at least one saturated or unsaturated and optionally substituted ring optionally comprising at least one heteroatom.

5. The dyeing method of claim 1, wherein the at least one entity chosen from ortho-diphenol and derivatives thereof is chosen from:
flavonols,
anthocyanidins,
anthocyanins or anthocyans,
orthohydroxybenzoates,
flavones,
hydroxystilbenes,
3,4-dihydroxyphenylalanine or a derivative thereof,
2,3-dihydroxyphenylalanine or a derivative thereof,
4,5-dihydroxyphenylalanine or a derivative thereof,
dihydroxycinnamates,
orthopolyhydroxycoumarins,
orthopolyhydroxyisocoumarins,
orthopolyhydroxycoumarones,
orthopolyhydroxyisocoumarones,
orthopolyhydroxychalcones,
orthopolyhydroxychromones,
orthopolyhydroxyquinones,
orthohydroxyxanthones,
1,2-dihydroxybenzene or a derivative thereof,
1,2,4-trihydroxybenzene or a derivative thereof,
1,2,3-trihydroxybenzene or a derivative thereof,
2,4,5-trihydroxytoluene or a derivative thereof,
proanthocyanidins,
proanthocyanins,
tannic acid, and
ellagic acid.

6. The dyeing method of claim 2, wherein the natural ortho-diphenol derivatives are chosen from natural ortho-diphenol derivatives present in at least one extract of an animal, bacterium, fungus, alga or plant.

7. The dyeing method of claim 6, wherein the at least one natural ortho-diphenol derivative is chosen from:
extracts of tea leaves,
extracts of rosemary leaves,
extracts of maté leaves,
extracts of fruits,
extracts of vegetables, and
extracts of tree wood.

8. The dyeing method of claim 7, wherein the at least one natural ortho-diphenol derivative is chosen from natural ortho-diphenol derivatives present in:
at least one extract of onion skin,
at least one extract of grape,
at least one extract of cocoa beans and/or pods,
at least one extract of pine bark, or
at least one extract of logwood.

9. The dyeing method of claim 1, wherein the at least one metal salt is chosen from manganese salts and zinc salts.

10. The dyeing method of claim 9, wherein the at least one metal salt is chosen from manganese halides, manganese sulfates, manganese phosphates, manganese nitrates, manganese perchlorates, manganese salts of carboxylic acids, zinc halides, zinc sulfates, zinc phosphates, zinc nitrates, zinc perchlorates, and zinc salts of carboxylic acids.

11. The dyeing method of claim 1, wherein the hydrogen peroxide or at least one system which generates hydrogen peroxide is chosen from hydrogen peroxide itself and urea hydrogen peroxide.

12. The dyeing method of claim 1, wherein the at least one system which generates hydrogen peroxide is chosen from:
a) urea hydrogen peroxide;
b) polymeric complexes which release hydrogen peroxide;
c) oxidases;
d) perborates; and
e) percarbonates.

13. The dyeing method of claim 1, wherein the at least one (bi)carbonate is chosen from alkali metal (bi)carbonates and alkaline earth metal (bi)carbonates.

14. The dyeing method of claim 1, wherein the method comprises first and second stages, the first stage comprising applying, to the keratinous fibers, a first composition comprising the at least one entity chosen from ortho-diphenol and derivatives thereof, the at least one metal salt, and the at least one hydrogen peroxide or at least one system which generates hydrogen peroxide, and the second stage comprising applying a second composition comprising the at least one (bi)carbonate, with at least one of the first and second compositions being aqueous.

15. The dyeing method of claim 1, wherein the method comprises first and second stages, the first stage comprising applying, to the keratinous fibers, a first composition comprising the at least one entity chosen from ortho-diphenol and derivatives thereof and the at least one metal salt, and the second stage comprising applying a second composition comprising the at least one (bi)carbonate and the at least one hydrogen peroxide or at least one system which generates hydrogen peroxide, with at least one of the first and second compositions being aqueous.

16. The dyeing method of claim 1, further comprising, just before applying the at least one (bi)carbonate, at least one of:
a) mechanically wiping the keratinous fibers; and
b) drying the keratinous fibers by heating.

17. The dyeing method of claim 16, wherein the keratinous fibers are not rinsed between the at least one of mechanical wiping and drying, and the applying the at least one (bi)carbonate.

18. A ready to use cosmetic composition for dyeing keratinous fibers comprising
i) at least one entity chosen from ortho-diphenol and derivatives thereof,
ii) at least one metal salt,
iii) hydrogen peroxide or at least one system which generates hydrogen peroxide,
iv) at least one (bi)carbonate,
and water in an amount greater than or equal to 50% by weight of the total weight of the composition.

19. A multicompartment device comprising from 2 to 5 compartments comprising from 2 to 5 compositions in which the ingredients
i) at least one entity chosen from ortho-diphenol and derivatives thereof, ii) at least one metal salt,
iii) hydrogen peroxide or at least one system which generates hydrogen peroxide,
iv) at least one (bi)carbonate,
and water are distributed, the water being present in at least one of the 2 to 5 compositions, the other 1 to 4 compositions being aqueous or pulverulent, and the water being present in a total amount greater than or equal to 50% by weight of the total weight of the 2 to 5 compositions.

* * * * *

UNITED STATES PATENT AND TRADEMARK OFFICE
CERTIFICATE OF CORRECTION

PATENT NO. : 7,857,865 B2  
APPLICATION NO. : 12/637236  
DATED : December 28, 2010  
INVENTOR(S) : Guerin et al.

Page 1 of 1

It is certified that error appears in the above-identified patent and that said Letters Patent is hereby corrected as shown below:

On the Title Page, Item (30), in the "Foreign Application Priority Data",
"08 58557" should read --0858557--.

In claim 14, column 26, lines 32-33, delete the line break between "(bi)" and "carbonate," (should read --(bi)carbonate,--).

In claim 17, column 26, lines 51-52, delete the line break between "(bi)" and "carbonate." (should read --(bi)carbonate.--).

Signed and Sealed this
Twenty-sixth Day of April, 2011

David J. Kappos
*Director of the United States Patent and Trademark Office*